US008834854B2

(12) United States Patent
Fisher et al.

(10) Patent No.: US 8,834,854 B2
(45) Date of Patent: Sep. 16, 2014

(54) ORAL TREATMENT COMPOSITIONS AND RELATED METHODS OF MANUFACTURE

(75) Inventors: Jeffrey J. Fisher, Ada, MI (US); Debra C. Soliz, Grand Rapids, MI (US)

(73) Assignee: Ranir, LLC, Grand Rapids, MI (US)

( * ) Notice: Subject to any disclaimer, the term of this patent is extended or adjusted under 35 U.S.C. 154(b) by 739 days.

(21) Appl. No.: 12/370,845

(22) Filed: Feb. 13, 2009

(65) Prior Publication Data

US 2009/0214450 A1   Aug. 27, 2009

Related U.S. Application Data

(60) Provisional application No. 61/030,729, filed on Feb. 22, 2008.

(51) Int. Cl.
| *A61K 8/365* | (2006.01) |
| *A61P 1/02* | (2006.01) |
| *A61Q 11/00* | (2006.01) |
| *A61K 8/34* | (2006.01) |
| *A61K 8/04* | (2006.01) |
| *A61K 8/25* | (2006.01) |

(52) U.S. Cl.
CPC . *A61K 8/25* (2013.01); *A61Q 11/00* (2013.01); *A61K 8/345* (2013.01); *A61K 8/042* (2013.01)
USPC .......................................... 424/53; 433/215

(58) Field of Classification Search
CPC ................................................... A61K 8/0208
USPC .................................................... 424/53, 130
See application file for complete search history.

(56) References Cited

U.S. PATENT DOCUMENTS

| 4,348,378 | A | * | 9/1982 | Kosti .......................... 424/9.71 |
| 4,788,052 | A | * | 11/1988 | Ng et al. ........................ 424/53 |
| 5,376,006 | A | | 12/1994 | Fischer |
| 5,409,631 | A | | 4/1995 | Fischer |
| 5,575,654 | A | | 11/1996 | Fontenot |
| 5,746,598 | A | | 5/1998 | Fischer |
| 5,985,249 | A | | 11/1999 | Fischer |
| 6,312,671 | B1 | | 11/2001 | Jensen et al. |
| 6,322,774 | B1 | | 11/2001 | Jensen et al. |
| 6,432,388 | B1 | * | 8/2002 | Alvarez Hernandez ........ 424/50 |
| 6,730,316 | B2 | | 5/2004 | Chen |
| 6,860,736 | B2 | | 3/2005 | Allred et al. |
| 2004/0146837 | A1 | * | 7/2004 | Andersen ...................... 433/215 |
| 2005/0036956 | A1 | | 2/2005 | Fei et al. |
| 2005/0036957 | A1 | * | 2/2005 | Prencipe et al. ................ 424/53 |
| 2006/0062744 | A1 | * | 3/2006 | Lokken ........................... 424/53 |

FOREIGN PATENT DOCUMENTS

| CA | 2375093 | 1/2001 |
| EP | 0535816 | 4/1993 |
| WO | 2008014096 | 1/2008 |

OTHER PUBLICATIONS

Canadian Office Action, Canadian Application No. 2,654,844, Aug. 23, 2010.
Annunziata et al., Effect of polyethylene glycol on a liquid-liquid phase transition and aqueous protein solutions, PNAS vol. 99, No. 22, pp. 14165-14170 (2002).

* cited by examiner

*Primary Examiner* — Walter Webb
(74) *Attorney, Agent, or Firm* — Warner Norcross & Judd LLP

(57) ABSTRACT

An oral treatment composition that includes a carrier, an active agent and a silicon dioxide compound. The active agent can be a variety of compositions, such as dental whitening or bleaching agents, desensitizing agents, antimicrobials, antiplaque agents, remineralizing agents, anti-tartar agents, mouth fresheners, and anesthetics. Optionally, a processing aid can be added to the composition to streamline manufacture of the gel. The composition can be formed as a bead in a dental tray so that when a user applies the dental tray to their dental arch, the bead readily spreads over the surfaces of the teeth without the user having to supply significant force to achieve such spreading.

15 Claims, 2 Drawing Sheets

ORAL TREATMENT COMPOSITIONS AND RELATED METHODS OF MANUFACTURE

CROSS-REFERENCE TO RELATED APPLICATION

This application claims benefit of U.S. Provisional Application No. 61/030,729, filed Feb. 22, 2008, which is incorporated by reference herein.

BACKGROUND OF THE INVENTION

The present invention relates to oral treatment products, and more particularly to oral treatment devices, related compositions to treat a subject's teeth, and related methods of manufacture of the compositions.

Many people desire to have whiter, brighter teeth. Accordingly, the oral care industry has developed a variety of products that contact the teeth and/or gums to provide a desired effect, such as whitening the teeth. An example of a whitening product is a rigid plastic dental tray including a trough configured for placement over a user's dental arch. A bead of extruded treatment composition including a whitening agent, such as peroxide, is disposed within the trough so that the composition theoretically contacts the teeth adequately when the tray is placed over the teeth.

Frequently, however, the treatment composition of these whitening products is formulated so that the bead will not liquefy when stored for long periods or in warm temperatures. As a result, when at normal room temperature, the treatment composition beads of such whitening products usually are a semi-solid to solid rubbery mass, which is resistant to spreading or significant deformation. Such a bead poses an issue for a user when applying the dental tray because the user must apply significant force to deform the bead enough so that the composition spreads across the teeth, and also penetrates the interproximal spaces between adjacent teeth. With sensitive or structurally compromised teeth, this can be painful or can physically damage the teeth.

One attempt to address the issue with semi-solid treatment composition beads is presented in U.S. Pat. No. 6,860,736 to Allred, which is hereby incorporated by reference in its entirety. Allred discloses a thin and flexible dental tray that is coated with a dental treatment composition forming a thin layer substantially covering the interior of the tray (replacing conventional, linear beads). This composition solidifies sufficiently to form an endoskeleton, which physically supports the walls of the dental tray, helping it maintain a tray like configuration before use. This endoskeleton is a substantially solid, but formable material, which provides support to the dental tray of Allred.

Due to its substantially solid state, however, the Allred endoskeleton is in a thick, relatively unspreadable putty like or rubbery form, which can be difficult to deform and spread over the teeth adequately. Indeed, to ensure that the endoskeleton adheres to the teeth, an adhesion agent, such as carboxypolymethylene or a polyvinyl pyrrolidone polymer is added to the Allred composition, which can add to the cost, processing time and chemical complexity of the composition.

SUMMARY OF THE INVENTION

The present invention provides a oral treatment composition used to maintain an active ingredient in contact with the surface of a user's teeth. The composition is in the form of a tacky, readily spreadable viscous gel.

In one embodiment, the oral treatment composition can be formed as a bead within a substantially rigid, self supporting, yet flexible dental tray, so that when a user applies the dental tray to their dental arch, the bead of the composition readily spreads over the surfaces of the teeth, as well as penetrates the interproximal spaces between teeth, without the user having to supply significant force to achieve such spreading.

In another embodiment, the oral treatment composition can include a matrix of a carrier, an active agent and a silicon dioxide, which matrix is at least partially responsible for the physical tacky, readily spreadable properties of the viscous gel composition.

In yet another embodiment, the oral treatment composition can be formulated to whiten or bleach a user's teeth. In this embodiment, the matrix active agent can be, for example, hydrogen peroxide, carbamide peroxide, chlorites, and combinations thereof, which exert a dental bleaching activity on the teeth to which the composition is applied. Optionally, the active agent can be hydrogen peroxide present in a range of about 1% to about 20% by weight of the final composition.

In a further embodiment, the oral treatment composition matrix can include as a carrier a polyol, for example, glycerin. Optionally, the carrier can be glycerin present in range of about 30% to about 80% by weight of the final composition.

In yet a further embodiment, the oral treatment composition matrix can include as its silicon dioxide component silica, which is admixed with the other ingredients of the composition. Optionally, the silica can be provided in powdered form, crystalline form, or fumed form, and can be present in a range of about 3% to about 16% by weight of the final composition.

In yet another, further embodiment, the oral treatment composition matrix can include a processing aid which enables the manufacture of the composition as a one-part gel. The processing aid can be a surfactant including at least one hydroxyl group and a hydrophilic-lipophilic balance (HLB) value of greater than about 4. The surfactant can be, for example, a polysorbate surfactant, such as polysorbate 20. Optionally, the processing aid can be polysorbate 20 present in range of about 0% to about 3% by weight of the final composition.

The present invention also provides a method of manufacturing a oral treatment composition in the form of a tacky, readily spreadable viscous gel. The method includes: providing a carrier, adding an active agent, optionally adding additional components, adding a silicon dioxide component, wherein the carrier, active agent, additional components and silicon dioxide components form a thin, viscous, liquid solution, and adding a processing aid to the liquid solution, the processing aid reacting with the liquid solution to create a matrix of the carrier, active agent and silicon dioxide so that the resulting oral treatment composition is in the form of a tacky, readily spreadable viscous gel.

In a specific embodiment of the method, the carrier, active agent, silicon dioxide and processing aid can be those discussed above in connection with the embodiments of the composition. Optionally, the carrier can be glycerin, the active agent can be hydrogen peroxide, the silicon dioxide component can be powdered silica, and the processing aid can be polysorbate 20.

In yet another embodiment the oral treatment composition in the form of a tacky, readily spreadable viscous gel, can be formed in a two-part gel process. The process includes: preparing a first part including a mixture of a carrier, such as glycerin, and silicon dioxide; preparing a second part including a mixture of silicon dioxide and an active agent, such as hydrogen peroxide; and mixing the first part and the second part together to form the final composition, which is in the form of a tacky, readily spreadable viscous gel. Optionally, the final composition can be substantially free or free of processing aids.

The present invention also provides a method of preparing a pre-filled oral treatment tray by dispensing a bead of oral treatment composition onto a oral treatment tray, terminating the bead of oral treatment composition, placing the filled dental treatment tray in a blister pack recess, and sealing the dental treatment tray within the blister pack recess. The method does not require the use of a pinching or cutting device to terminate the bead during the filling process, because of the consistency of the composition. This enables the dental tray to be filled in a simply one-step process.

The oral treatment composition provides a simple and efficient tacky, spreadable viscous gel, which readily spreads over the surfaces of the teeth, as well as penetrates the interproximal spaces between teeth, without the user having to supply significant force to achieve such spreading. In turn, the composition is well suited for all types of users, even those with sensitive teeth, or teeth that may be structurally compromised. Moreover, because the composition is so readily spreadable, it can be easily and quickly applied via a pre-filled dental tray, and due to its extensive spreading over the surfaces of the teeth, it provides a whitening effect to substantially all portions of the teeth to which it is applied. As a result, users experience a better whitening treatment, and in some cases, in less time. Finally, due to the unexpected discovery of the way in which the ingredients of the oral treatment composition react, the inventive method provides a simple, ordered mixing technique that enables the production of a one-part gel that is tacky, readily spreadable and viscous.

These and other objects, advantages and features of the invention will be more readily understood and appreciated by reference to the detailed description of the invention and the drawings.

DETAILED DESCRIPTION OF THE INVENTION

I. Overview and Definitions

Figure 1:
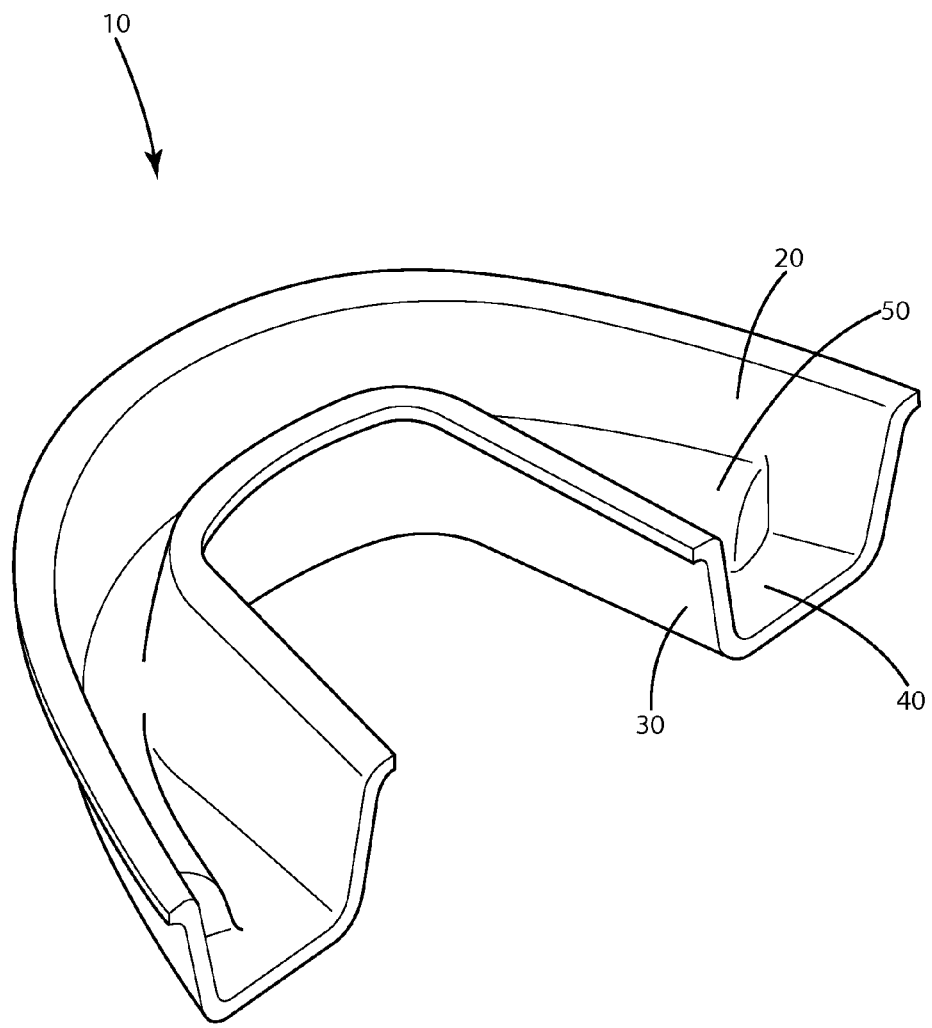
FIG. 1 is a perspective view of a oral product, a dental tray, including the oral treatment composition of one embodiment.

The present invention provides a oral treatment composition used to maintain an active ingredient in close proximity to surfaces and interproximal spaces of a user's teeth. The composition is a tacky, readily spreadable viscous gel. The tacky, readily spreadable viscous gel structure enables the oral treatment composition to temporarily maintain an active ingredient contained therein in close proximity to surfaces and interproximal spaces of a user's teeth. Because of this consistency, the oral treatment composition can also be formed as a bead within a substantially rigid, self supporting, yet flexible dental tray, so that when a user applies the dental tray to their dental arch, the bead of the composition readily spreads over the surfaces of the teeth, as well as penetrates the interproximal spaces between teeth, without the user having to exert significant force to achieve such spreading.

As used herein, the term "tacky," when referring to a composition, refers to a characteristic such that the composition is sticky to the touch, and readily able to at least temporarily adhere to a surface to which the composition or gel is brought into contact with, for example, a tooth surface. The tacky composition can also be capable of temporarily adhering to the surface of the user's teeth while also supporting a remaining portion of the composition, and/or dental tray, so that the composition, and consequently the dental tray, remain in contact with the tooth surface for an adequate treatment period as determined by those of skill in the art.

As used herein, the term "readily spreadable viscous gel," refers to a composition that has been formulated so that it does not readily flow by the force of gravity, but is viscous so that it can be spread with a low shear rate when applied to a tooth surface, for example, at a shear rate of about 0.01 to about 1 l/sec when the composition is applied in a bead form within a dental tray applied over a dental arch. In one embodiment, the composition gel has a consistency similar to peanut butter. A readily spreadable viscous gel is also viscous enough that it can be expressed through a nozzle orifice or other dispenser orifice at a moderate shear rate. In one embodiment, the shear rate in pumping or dispensing the composition in a bead form from a nozzle can be about 50 to about 5,000 l/sec.

As used herein, the term "dental tray" refers to an appliance having a tray-like configuration that facilitates placement of the device over at least a portion of a user's dental arch. A dental tray can include a front wall which engages the front surfaces of a user's teeth, a rear wall extending laterally from the front wall, either abruptly by at least one angle or non-abruptly by a curved part, configured to engage the rear surfaces of a user's teeth. The dental tray can also include a trough between the front and rear walls. A dental tray can also be configured so that a portion of it engages the incisal or occlusal portions of the user's teeth.

As used herein, "pre-filled dental tray" refers to a dental tray including a quantity of composition that is filled by a manufacturer before distribution to an end user. In one embodiment, the dental tray includes a bead of composition that is filled by a manufacturer before distribution to an end user.

As used herein, "bead," when referring to a quantity of composition refers to a small globular or cylindrical body of the composition. The bead generally maintains its shape after being extruded or dispensed.

As used herein, "substantially rigid, self supporting, yet flexible," when referring to a dental tray, refers to a tray that self-supports its components, for example, its walls, in a desired configuration, but that is able to be flexed to at least partially deform to conform to an user's arch sufficiently to apply a oral treatment composition within the tray to an user's teeth.

II. Oral Treatment Compositions and Products

The oral treatment composition according to the invention includes a matrix of a carrier, an active agent and a silicon dioxide. In general, the matrix creates the physical tacky, readily spreadable properties of the viscous gel composition. Optional processing aids can be added to the composition in manufacture to produce a one-part gel. Additional components can be added to the matrix to provide a oral treatment composition having other desired properties. The composition can be disposed in a pre-filled dental tray to facilitate use by consumers. The following are examples of the carriers, active agents, and the silicon dioxide in the matrix, along with optional processing aids, optional additional components, and examples of dental trays.

A. Carriers

Examples of carriers that can be used in the oral treatment composition matrix can include, but are not limited to, polyols, such as glycerin, sorbitol, mannitol, other sugar alcohols ("polyols"), propylene glycol, 1,3-propanediol, polyethylene glycol, polyethylene oxide, and polypropylene glycol. Optionally, the carrier can be glycerin present in range of about 30% to about 80% by weight of the final composition. In one embodiment, the carrier can be present in a range having a lower end of about 35%, 40%, 45%, 50%, 55%, or 60%, and an upper end of about 60%, 65%, 70%, or 75%. Further optionally, the carrier can be glycerin, and can be present in an amount of about 55.05%.

B. Active Agents

Examples of active agents that can be used in the oral treatment composition can include, but are not limited to, dental whitening or bleaching agents, desensitizing agents, antimicrobials, anti-plaque agents, remineralizing agents, anti-tartar agents, mouth fresheners, and anesthetics. Specific dental whiteners include, but are not limited to, hydrogen peroxide, carbamide peroxide, calcium peroxide, hypochlorites, peroxy acids, metal chlorites, chlorites, and combinations thereof, which exert a dental bleaching activity on the teeth to which the composition is applied. Optionally, the active agent can be hydrogen peroxide present in a range of about 1% to about 20% by weight of the final composition. In one embodiment, the active agent can be present in a range having a lower end of about 3%, 4%, 5%, 10% or 15% and an upper end of about 15%, 18%, 19%, or 20%. Further optionally, the active agent can be hydrogen peroxide present in an amount of about 10.50%.

C. Silicon Dioxide Components

Examples of silicon dioxide components that can be used in the oral treatment composition include, but are not limited to, silica, or other comparable inert, inorganic non-toxic thickening compounds. Optionally, the silica can be provided in powdered, fumed, and/or crystalline form, and can be present in a range of about 3% to about 16% by weight of the final composition. In one embodiment, the silicon dioxide component can be present in a range having a lower end of about 4%, 5%, 8%, or 10% and an upper end of about 12%, 13%, 14%, or 15%. Further optionally, the silicon dioxide component can be fumed silica present in an amount of about 8.00%.

In particular embodiments, the silicon dioxide and carrier can be provided in particular ratios. For example, the silicon dioxide can be silica, and the carrier can be glycerin, where these components are in the ratio ranges of about 0.04:0.3 (silica:glycerin).

D. Processing Aids

The oral treatment composition matrix can include an optional processing aid that enables the manufacture of the composition as a one-part gel. In other words, the composition can be manufactured by adding ingredients individually and sequentially, without having to admix certain ingredients together before combining the admixed ingredients with further ingredients. The processing aid can be a surfactant including at least one hydroxyl group and a hydrophilic-lipophilic balance (HLB) value of greater than about 4. Examples of surfactants include, but are not limited to, a polysorbate surfactant, such as polysorbate 20, polysorbate 60, polysorbate 80, and other polyoxyethylene derivatives of sorbitan monolaurate, a polaxamer, such as poloxamer 407, other polyoxypropylene derivatives, sodium monolaurate, laureth-6 carboxylic acid, and combinations thereof. Optionally, the processing aid can be polysorbate 20 present in range of about 0% to about 3% by weight of the final composition.

In one embodiment, the processing aid can be present in a range having a lower end of about 0.1%, 0.5%, 1%, or 1.5% and an upper end of about 1.5%, 2%, 2.5%, or 2.75%. Further optionally, the processing aid can be polysorbate 20 present in an amount of about 1.68%.

In particular embodiments, the processing aid and silicon dioxide can be provided in particular ratios. For example, the processing aid can be a surfactant as noted above, and the silicon dioxide can be silica, with these components in the ratio ranges of about 0.02:0.3, optionally about 0.1:0.25 (surfactant:silica). As a more specific example, the processing aid can be polysorbate 80, and the silicon dioxide can be silica, with these components in the ratio ranges of about 0.02:0.3, optionally about 0.1:0.25 (polysorbate:silica).

E. Additional Components

The oral treatment compositions also can include other components that provide additional desired properties. Examples of such components include, but are not limited to, fillers, water, whitener stabilizers, such as EDTA, disodium EDTA, and salts thereof, citric acid and salts thereof, phosphoric acid and salts thereof, phenolphosphonic acid and salts thereof, gluconic acid and salts thereof, alkali metal pyrophosphates, alkali metal polyphosphates, alkyl sulfates; neutralizing agents, such as sodium hydroxide and triethanolamine, colorants, flavorants, such as vanilla, rose, and mint, sweeteners, such as saccharin, sodium saccharin, and other artificial sweeteners; stabilizers, such as xanthum gum, and the other components known to those of skill in the art as being useful in this type of composition. In one embodiment, the composition can include at least one of the additional components, each present in a range having a lower end of about 0.1%, 0.5%, 1%, 1.5%, 2%, 5%, or 10% and an upper end of about 1%, 1.5%, 2%, 2%, 5%, 7%, 10%, 15%, 20%, 25%, 30%, 35%, or 40%. In one embodiment, the following additional components are included in the compositions: water is present in an amount of about 19.50%; sodium saccharin is present in an amount of about 1.5%; citric acid is present in an amount of about 1.14%; disodium EDTA is present in an amount of about 1.08%; a flavoring ingredient is present in about 0.8%; and xanthum gum is present in an amount of about 0.75%.

In one embodiment, the oral treatment composition can be substantially free or free of tackifying agents. Tackifying agents can be used to adhere the composition to surfaces, such as tissue. For example, the composition can be substantially free or free of hydrophilic polymers, such as carboxypolymethylene, polyvinyl pyrrolidone, polyacrylates, polyacrylamides, polyethylene oxide, and combinations thereof.

F. A Dental Tray and Inclusion of Oral Treatment Compositions Therein

The oral treatment compositions of the embodiments above can be included in a dental tray, with the finished product being a pre-filled dental tray. An example of a whitening dental product, in the form of a pre-filled tray is illustrated in FIG. 1. There, the dental tray 10 includes a front wall 20, a rear wall 30, and a trough 40 having a "U" or "V" shape. The dental tray can be constructed from polyethylene, high density polyethylene, low density polyethylene, ultra low density polyethylene, polypropylene, polytetrafluoroethylene, paraffin, wax, foil, paraffin, ethylene-vinyl acetate, ethylene-vinyl alcohol, polyvinyl chloride, polyurethane, polyester, polycarbonate, polyamide and polyesteramide, combinations thereof, and other similar compounds.

A continuous bead of the oral treatment composition 50 can be disposed within the trough 40. Although shown as continuous, the bead may be broken as desired. Further, the bead of the oral treatment composition can be in the form of a tacky, readily spreadable viscous gel. Optionally, the bead itself provides no structural support to the dental tray. Further optionally, the bead can have a circular, semicircular, rectangular, oval, or other geometric cross section. The cross-sectional diameter or thickness of the bead can be about 0.5 mm to about 6 mm, optionally about 2 mm to about 5 mm.

III. Methods of Manufacturing Oral Treatment Compositions and Filling Dental Products The oral treatment composition can be prepared by mixing ingredients in a variety of orders, with a variety of different ingredients. Several exemplary embodiments will now be described.

In a first embodiment, the oral treatment composition can be mixed generally in two primary parts, which are then combined. This particular process yields what is called a two-part gel, which refers to the fact that two different primary parts are first mixed, then combined. In this embodiment, the two primary parts can be Part A, and Part B. In general, Part A can include a mixture of a carrier, such as glycerin, and silicon dioxide; and Part B can include a mixture of silicon dioxide and an active agent, such as hydrogen peroxide. Both of these Parts can be mixed together to form the final composition, which is in the form of a tacky, readily spreadable viscous gel. In a particular embodiment, Parts A and B can include the ingredients listed in Table I below, in the respective weight percentages. Of course, the ingredients and respective weight percentages can be altered to include those noted above as well or to provide alternative consistencies by altering the weight percentages of the individual ingredients.

TABLE I

| Ingredient | % by Weight |
|---|---|
| Part A | |
| Glycerin | 85.80% |
| Citric Acid | 1.69% |
| Disodium Edetate | 1.59% |
| Sodium Saccharin | 2.21% |
| Flavor | 1.17% |
| Fumed Silica | 7.55% |
| Total | 100.00% |
| Part B | |
| Fumed Silica | 8.26% |
| Hydrogen Peroxide (35% soln) | 91.74% |
| Total | 100.00% |

The process for mixing the Parts of Table I is as follows. For Part A, the citric acid, disodium EDTA and sodium saccharin are added to the glycerin and mixed. The flavor is added and mixed with the other ingredients. The fumed silica is added and mixed with the other ingredients. At this point, the Part A mixture can be a thick solution which exhibits a somewhat high viscosity of about 2,000,000 cps to about 10,000,000 cps. For part B, the fumed silica is added to the hydrogen peroxide and mixed. At this point, the Part B mixture can be a thick solution which exhibits a somewhat high viscosity of about 1,000,000 cps to about 5,000,000 cps.

Thereafter, the Part A and Part B are mixed together. In some cases, because both solutions are thick, it can take extra time or mixing forces to mix Part A and Part B. After the Part A and Part B of Table I are mixed, the resulting Formulation of the oral treatment composition can include the ingredients listed in Table II below, in the respective weight percentages. Of course, the ingredients and respective weight percentages can be altered to include those noted above as well.

TABLE II

| Ingredient | % by Weight |
|---|---|
| Formulation | |
| Glycerin | 58.18% |
| Citric Acid | 1.15% |
| Disodium Edetate | 1.08% |
| Sodium Saccharin | 1.39% |
| Fumed Silica | 7.79% |
| Hydrogen Peroxide (35% soln) | 29.62% |
| Flavor | 0.79% |
| Total | 100.00% |

The resulting Formulation in Table II of the oral treatment composition is in the form of a tacky, readily spreadable viscous gel. It is believed that the glycerin, hydrogen peroxide and silica (that is the carrier, the active agent and the silicon dioxide) form the matrix that enables the gel to be tacky, readily spreadable and viscous.

In a second embodiment, the oral treatment composition can be mixed generally in a somewhat ordered manner so that preliminary mixing of two primary parts can be avoided. Optionally, a processing aid can be used to streamline the process and yet still result in a oral treatment composition in the form of a tacky, readily spreadable viscous gel. In general, a carrier, such as glycerin, and an active agent, such as hydrogen peroxide are mixed to form a thin solution. The silicon dioxide, such as silica, is then added to this mixture, which results in a relatively thin solution, having a viscosity of about 500 cps to about 20,000 cps. Thereafter, a processing aid, such as polysorbate 20, can be added to thicken the mixture and form the oral treatment composition in the form of a tacky, readily spreadable viscous gel.

In a particular embodiment, the ingredients of the composition are listed in Table III below, in the respective weight percentages. Of course, the ingredients and respective weight percentages can be altered to include alternatives known to those of skill in the art.

TABLE III

| Ingredient | % by Weight |
|---|---|
| Final Formulation | |
| Glycerin | 55.05% |
| Water | 19.50% |
| Hydrogen Peroxide | 10.50% |
| Silica | 8.00% |
| Polysorbate 20 | 1.68% |
| Sodium Saccharin | 1.50% |
| Citric Acid | 1.14% |
| Disodium EDTA | 1.08% |
| Flavor (art. Vanilla Rose Mint) | 0.80% |
| Xanthan Gum | 0.75% |
| Total | 100.00% |

The process for mixing the Final Formulation in the above Table III can be ordered, with the ingredients added in the following sequence: glycerin to water; hydrogen peroxide to that mixture; citric acid, disodium EDTA and sodium saccharin; silica; flavor; and glycerin/flavor (up to this point, the mixture is a relatively thin solution); and finally polysorbate 20. The resulting Formulation in Table III of the oral treatment composition is in the form of a tacky, readily spreadable viscous gel. Due to the combination of the carrier, such as glycerin and active ingredient, such as hydrogen peroxide, before introduction of the silicon dioxide, such as silica, to either, the combination does not prematurely thicken, which can, in some limited cases, cause difficulty in subsequent mixing.

After the oral treatment composition is manufactured, it can be joined with a dental product, and that dental product can be packaged for sale to end consumers. In one embodiment, the oral treatment composition is dispensed as a bead into a dental tray to form a pre-filled dental tray. Specifically, the oral treatment composition in bulk form can be pumped under pressure through a dispensing nozzle, sized with an outlet orifice of about 0.02" to about 0.25", optionally about 0.125". During such dispensing, the shear exerted on the composition is about 100 to about 1000 l/sec. The nozzle can be positioned so that it dispenses a bead 50 of the composition into the dental tray 10 (FIG. 1). Due to the composition being in tacky, readily spreadable viscous gel, the bead can be terminated simply by stopping the pumping of the composition through the nozzle, and distancing the nozzle and tray from one another. Thus, if desired, the composition can be dispensed in a bead in a single tray without having to cut or pinch off the bead in terminating that bead. For example, the bead can be severed simply by moving the nozzle away from the surface to which the bead is applied by about 1" to about 3" so that the bead on the surface separates from the nozzle. In this manner, the bead need not be severed with a secondary cutting device, such as a knife or pincher.

With the dental tray being pre-filled with the composition, the tray can be placed in a blister pack recess, and sealed over with a foil or other tamper evident seal. This blister pack construction can then be placed in a package of multiple pre-filled trays for further processing and distribution. A number of trays in a single package can provide a kit equal to the number of sessions required to achieve a desired effect with the kit, for example, whitening the teeth.

As desired, the oral treatment composition can be provided in a tube or other manual dispenser for dispensation by an end consumer into a dental tray or other dental product.

IV. Methods of Using Oral Treatment Compositions with Dental Products

The oral treatment composition can be used in a variety of ways. Several exemplary embodiments will now be described.

In a first embodiment, a pre-filled dental tray including the oral treatment composition described above can be accessed by a user by removing the foil from the blister, and the tray from the blister. The tray, including the oral composition can be applied to the upper or lower dental arch of the user, with the teeth generally fitting within the trough of the tray. Due to tacky, readily spreadable viscous gel form of the composition, when the user applies the dental tray to their dental arch, the bead of the composition readily spreads over the surfaces of the teeth, as well as penetrates the interproximal spaces between teeth, without the user having to supply significant force to achieve such spreading. In one example, a shear rate of about 0.01 to about 0.1 l/sec is produced as the user placed the dental tray over the arch as the composition spreads over the teeth.

The dental tray can be worn for several minutes to several hours. In one embodiment, a treatment session can last for about 10 to about 30 minutes. Longer treatment sessions of about 30 minutes to about 2 hours are also contemplated. Generally, the tackiness of the gel can be designed to hold the dental tray on the teeth via adhesion only for about 10 minutes, optionally about 20 minutes, further optionally about 30 minutes or longer.

Treatment sessions can be repeated to obtain a desired degree of treatment. When used as a whitening dental product, the composition can be used once a day for 1 to 3 days to create visibly whiter teeth. For further whitening, the composition can be used once a day for 7 to 10 days. These treatment sessions can be repeated every six months or other frequency depending on the desired effect. In the case of bleaching devices, a clinical whitening effect has been observed after only 1 to 3 whitening sessions.

In another embodiment, a pre-filled tube of oral treatment composition, as described above, can be opened by the user. The user dispenses a bead of the oral treatment composition into a dental tray or other dental product. The user stops dispensing the composition when a sufficient amount of composition is in the dental tray or product. In order to stop dispensing the user only needs to stop exerting pressure on the tube or dispenser, there is no need to cut or otherwise pinch off the bead. After the dental tray or product has been filled by the user, the user inserts the dental tray or product into their mouth as described above with regard to the pre-filled tray.

V. Examples

The following are examples of the performance of oral treatment compositions according to the invention. These examples are provided by way of example, not by limitation, to illustrate compositions and products that can be useful for maintaining contact between an active agent and a person's teeth and/or gums.

A. Example 1

In this example, the oral treatment composition of Table III was tested in vitro to determine whitening efficacy. The testing was performed on bovine teeth using the following procedure for the composition. First, the initial color of tooth measured and recorded using an X-Rite ShadeVision System (available from X-Rite, Inc. of Grand Rapids, Mich.). Three teeth were wetted with artificial salvia and then inserted into the composition in a whitening tray. Great effort was taken to be sure that gel covered the front of the tooth. All teeth remained in the tray for 30 minutes, then were rinsed with water. The teeth were then rewetted with saliva and inserted into fresh gel in a new tray. This procedure was repeated for a total of three 30 minute applications. The teeth were then measured with the ShadeVision System in its whitening value mode, and the values indicating the change in whiteness due to use of the composition was recorded as presented in Table IV below.

TABLE IV

| | X-Rite Whitening Value Change (This used the whitening values on the ShadeVision) | Delta E |
|---|---|---|
| tooth 1 | 2 | 3.02 |
| tooth 2 | 1 | 3.34 |
| tooth 3 | 1.5 | 3.03 |
| average | 1.5 | 3.13 |

These results confirm that the oral treatment composition perform extremely well at whitening teeth. It is believed that these exceptional results are at least in part due to the spreadability of the composition, and the fact that it easily coated the tooth surface.

B. Example 2

Figure 2:
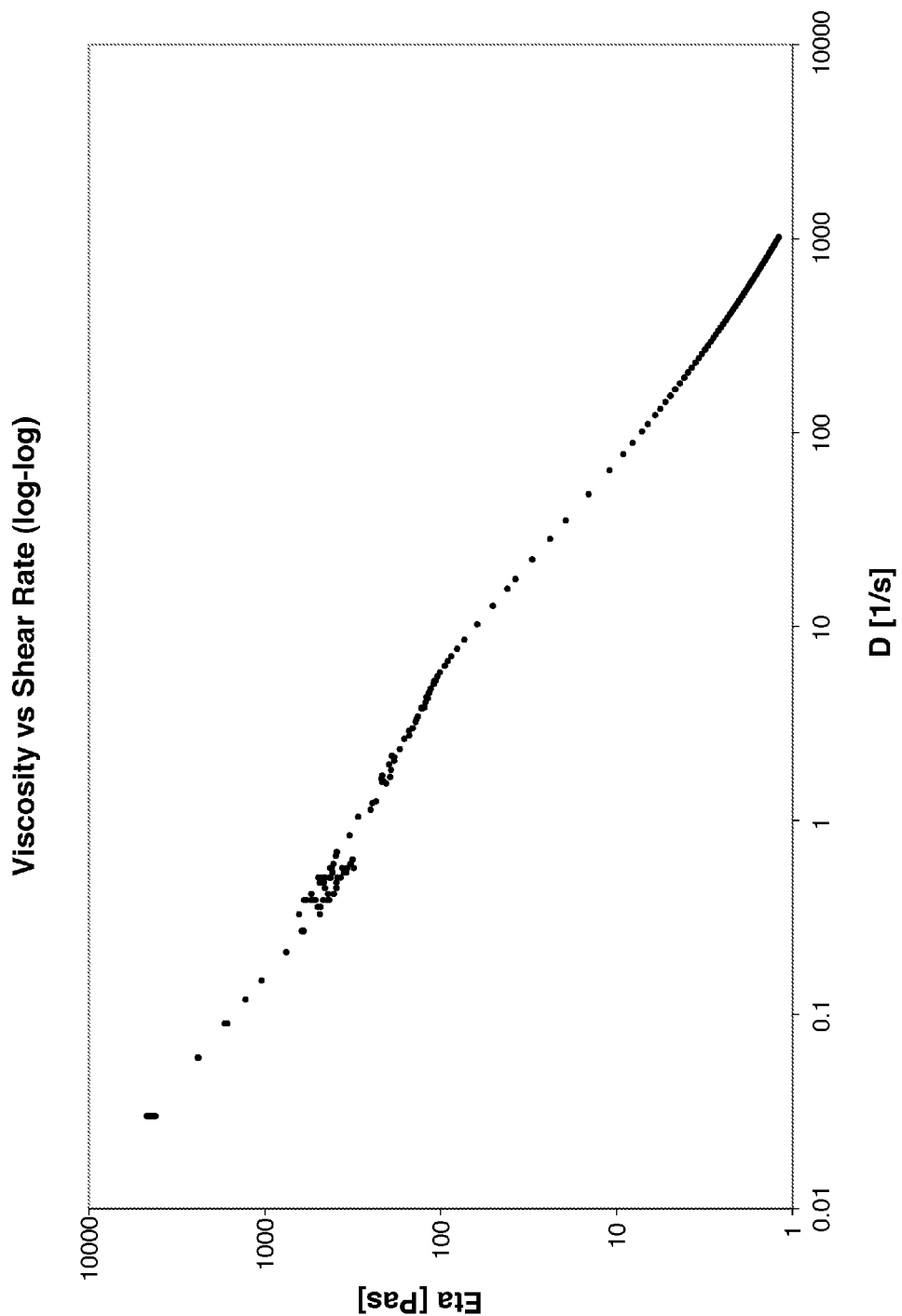
FIG. 2 is a graph illustrating viscosity versus shear rate of the oral treatment composition.

In this example, the oral treatment composition of Table III was tested to analyze the spreadability of the composition in terms of shear rate versus viscosity. To perform this test a Brookfield Rate/Shear Cone & Plate Rheometer utilizing a 25 mm, 2 degree cone was used. Viscosity was measured as shear and was ramped from 0 to 1,000 1/sec. The results of this test are expressed in the log-log graph at FIG. 2. The Y-Axis indicates viscosity in pascal second (Pa-s); and the X-axis indicates the shear rate in 1/sec. This data shows that the composition is readily spreadable because of its viscosity of 4,000 to 2,000 Pa-s (4,000,000 to 2,000,000 cP) or vice versa, when applied to the teeth. At this viscosity, the gel will spread well. Of course, the viscosity of the composition can be modified so that its lower end of the range can be about 400,000 centipoises, 750,000 centipoises, or 1,000,000 centipoises by, for example, adding more water or reducing silica content, or other methodologies for reducing viscosities.

The above description is that of the current embodiment of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The embodiments of the invention in which an exclusive property or privilege is claimed are defined as follows:

1. An oral treatment composition associated with a dental tray comprising:
    an orally administrable matrix including a carrier, an active agent, a processing aid, and a silicon dioxide, said orally administrable matrix in the form of a bead;
    a dental tray, said bead of orally administrable matrix disposed in the dental tray;
    wherein said matrix forms a tacky, spreadable gel having a viscosity of between about 4,000 Pa·s and about 2,000 Pa·s;
    wherein said active agent is hydrogen peroxide that functions as a whitening agent;
    wherein the orally administrable matrix is substantially free of hydrophilic polymers, including being substantially free of polyvinyl pyrrolidone;
    wherein the orally administrable matrix includes about 5% to about 40% water by weight of the oral treatment composition;
    wherein said silicon dioxide is present in a range from 4% to 10% by weight of the oral treatment composition;
    wherein said bead is adapted for application to a dental arch of a subject by application of the dental tray containing the bead to the dental arch of the subject;
    wherein said viscosity enables the active agent of said orally administrable matrix to be maintained in close proximity to surfaces and interproximal spaces between adjacent teeth of the subject.

2. The oral treatment composition of claim 1, wherein said carrier is selected from the group consisting of glycerin, sorbitol, mannitol, sugar alcohols, and 1,3-propanediol.

3. The oral treatment composition of claim 1, wherein said carrier is present in a range from about 30% to about 80% by weight of the oral treatment composition.

4. The oral treatment composition of claim 1, wherein said active agent is present in a range from about 1% to about 20% by weight of the oral treatment composition.

5. The oral treatment composition of claim 1, wherein said silicon dioxide is selected from the group consisting of silica in powdered form, crystalline form, and fumed form.

6. The oral treatment composition of claim 1, wherein said silicon dioxide is present in an amount of about 8% by weight of the oral treatment composition.

7. The oral treatment composition of claim 1, wherein the processing aid is a polysorbate surfactant, wherein the polysorbate surfactant and the silicon dioxide are mixed in a ratio of about 0.02:0.3 (polysorbate surfactant:silicon dioxide).

8. The oral composition of claim 1, wherein the processing aid is a surfactant selected from the group consisting of polysorbate 20, polysorbate 60, polysorbate 80, polyoxyethylene derivatives of sorbitan monolaurate, a polaxamer, polyoxyproplylene derivatives, sodium monolaurate, laureth-6 carboxylic acid, and combinations thereof.

9. A method of forming the oral treatment composition of claim 1, comprising:
    providing a carrier;
    adding an active agent;
    adding a silicon dioxide component, wherein the carrier, active agent, and silicon dioxide components form a thin, viscous, liquid solution; and
    adding a processing aid to the liquid solution after the liquid solution including the carrier, active agent, and silicon dioxide is formed, wherein the processing aid reacts with the liquid solution to create a matrix of the carrier, active agent and silicon dioxide so that the resulting oral treatment composition is in the form of the tacky, readily spreadable viscous gel.

10. A method of forming the oral treatment composition of claim 1, comprising:
    preparing a first part including a mixture of a carrier and a silicon dioxide;
    separately preparing a second part including a mixture of a silicon dioxide and an active agent; and
    mixing the first part and the second part together after the first part and second part are prepared to form the oral treatment composition, which is in the form of the tacky, readily spreadable viscous gel.

11. A method of using the oral treatment composition of claim 1 comprising:
    providing the orally administrable matrix in the form of a bead disposed in a dental tray;
    applying the dental tray to a dental arch of a subject so the orally administrable matrix spreads over a plurality of teeth as the dental tray is applied, wherein a shear rate of the matrix between the plurality of teeth and the dental tray is 0.01 l/sec to 0.1 l/sec as the dental tray is applied; and
    retaining the dental tray adjacent the dental arch for 10 minutes or longer to promote a whitening effect on the plurality of teeth;
    wherein said orally administrable matrix is substantially free of hydrophilic polymers, wherein said silicon dioxide is present in a range from 3% to 16% by weight of the orally administrable matrix, and wherein said orally administrable matrix is in the form of a bead disposed in a dental tray.

12. The oral treatment composition of claim 1 comprising;
water present in an amount of about 15% to about 35%;
a polysorbate surfactant present in an amount of about 0.1% to about 2.75% by weight of the oral treatment composition;
an acid present in an amount of about 1.0% to about 5.0% by weight of the oral treatment composition,
flavoring present in an amount of about 0.1% to about 5% by weight of the oral treatment composition; and
a stabilizer present in an amount of about 0.1% to about 5% by weight of the oral treatment composition,
wherein said carrier includes glycerin present in an amount of about 45% to about 65% by weight of the oral treatment composition,
wherein said hydrogen peroxide is present in an amount of about 5% to about 20% by weight of the oral treatment composition.

13. The oral treatment composition of claim 12,
wherein the glycerin is present in an amount of 55.05% by weight of the oral treatment composition,
wherein the water is present in an amount of 19.50% by weight of the oral treatment composition,
wherein the polysorbate surfactant is present in an amount of 1.68% by weight of the oral treatment composition,
wherein the hydrogen peroxide is present in an amount of 10.50% by weight of the oral treatment composition;
wherein the silica dioxide is present in an amount of 8% by weight of the oral treatment composition,
wherein the acid is citric acid present in an amount of 1.14% by weight of the oral treatment composition,
wherein the flavoring is present in an amount of 0.80% by weight of the oral treatment composition,
wherein the stabilizer is xanthan gum present in an amount of 0.75% by weight of the oral treatment composition.

14. The oral treatment composition of claim 1, wherein the gel is spreadable at a shear rate of between about 0.01 l/sec to about 1 l/sec.

15. The oral treatment composition of claim 1, wherein the composition provides a delta whitening on a shade scale of between about 3.02 and about 3.13.

* * * * *